United States Patent [19]

Hammond et al.

[11] Patent Number: 5,330,973
[45] Date of Patent: Jul. 19, 1994

[54] LIPOPEPTIDE DERIVATIVES

[75] Inventors: Milton L. Hammond, Somerville; Robert E. Schwartz, Westfield; James M. Balkovec, North Plainfield, all of N.J.

[73] Assignee: Merck & Co., Inc., Rahway, N.J.

[21] Appl. No.: 495,198

[22] Filed: Mar. 19, 1990

[51] Int. Cl.$^5$ .......................... C07K 5/12; C07K 7/06; A61K 37/02

[52] U.S. Cl. ...................................... 514/11; 530/317; 514/9

[58] Field of Search ...................... 530/317; 514/11, 9

[56] References Cited

U.S. PATENT DOCUMENTS

| | | | |
|---|---|---|---|
| 4,288,549 | 9/1981 | Breck et al. | 435/119 |
| 4,293,490 | 10/1981 | Abbott et al. | 530/317 |
| 4,293,491 | 10/1981 | Debono et al. | 530/317 |
| 4,320,054 | 3/1982 | Abbott et al. | 530/317 |
| 4,322,338 | 3/1982 | Abbott et al. | 530/317 |
| 4,791,100 | 12/1988 | Kramer et al. | 514/12 |
| 4,931,352 | 6/1990 | Fromtling et al. | 530/317 |

FOREIGN PATENT DOCUMENTS

| | | |
|---|---|---|
| 032009 | 11/1280 | European Pat. Off. . |
| 0431350A1 | 6/1991 | European Pat. Off. . |
| 0462531A1 | 12/1991 | European Pat. Off. . |

OTHER PUBLICATIONS

Traber et al., Helv. Chim. Acta 62, 4, 1252–67 (1979).
Pache, W. et al., 13th International Congress Chemotherapy (1983), PS 4.8/3, Part 115, Abstract No. 10; also references in Ann. Reports in Med. Chem. 19, Sec. III, 130–131.

Primary Examiner—Merrell C. Cashion, Jr.
Assistant Examiner—S. G. Marshall
Attorney, Agent, or Firm—Elliott Korsen; Mark R. Daniel

[57] ABSTRACT

The present invention is directed to water-soluble derivatives of antibiotic lipopeptides. The derivatives have good solubility properties in aqueous medium, rendering them more useful as therapeutic agents.

12 Claims, No Drawings

LIPOPEPTIDE DERIVATIVES

The present invention is directed to a compound having the formula

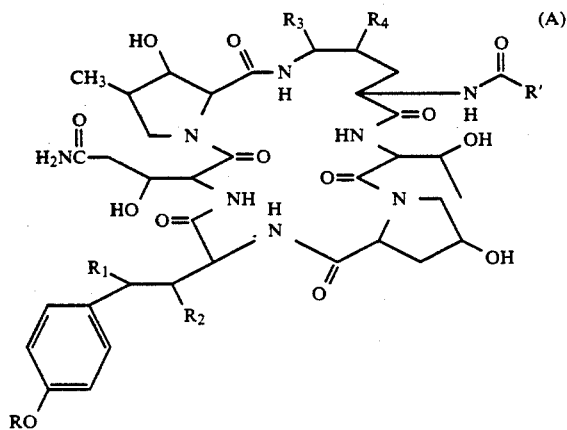

Wherein $R_1$, $R_2$, $R_3$ and $R_4$ are independently H or OH. R is an acyl, phosphono or sulfo radical which possesses a charged group at a neutral pH, R' is $C_5$-$C_{23}$ alkyl, $C_5$-$C_{23}$ alkenyl, $C_5$-$C_{23}$ alkynyl or aryl.

The preferred compounds are those which may be represented by the formula

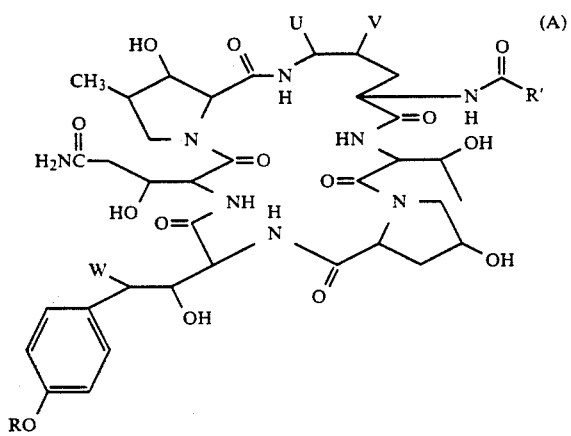

wherein, R is an acyl, phosphono or sulfo radical which possesses a charged group at neutral pH; R' is a $C_5$-$C_{23}$ alkyl, $C_5$-$C_{23}$ alkenyl, $C_5$-$C_{23}$ alkynyl or aryl; U, V and W are independently H or OH and selected from those in which (1) U, V and W are all OH; (2) U and W are H and V is OH; (3) U and V are H and W is OH; and (4) U is H and V and W are OH.

The alkyl, alkenyl and alkynyl groups may be either straight chain or branched. When alkenyl or alkynyl, from 1 to 3 unsaturated groups may be present. Especially preferred are $C_{13}$ to $C_{17}$ groups such as tridecyl, pentadecyl, 8,11-heptadecadienyl, 7-pentadecenyl, 10-heptadecenyl, 9,11-dimethyltridecyl, and the like.

By the expression "aryl" is meant preferably phenyl or substituted phenyl. Substituents may be alkyl, alkyloxy, alkylthio, alkylamino. The carbon content of the alkyl is from 1 to 10. The preferred substituted aryl may be represented by

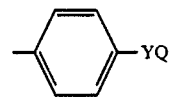

wherein Y is $CH_2$, S, O or NH and Q is $C_{6-10}$alkyl. A preferred member of this group is a radical in which Y is O, and Q is $C_8H_{17}$.

"Acyl, phosphono or sulfo radicals which possess a charged group at neutral pH" include those which may be an anion from an acid or a cation form of an amine base and may be further defined as follows:

(1) $PO_3AH$ wherein A is H, $C_1$-$C_6$ alkyl, phenyl or substituted phenyl in which the substituent is alkyl, alkyloxy, alkylthio, or alkylamino, or a cation salt thereof;

(2) $SO_3H$ or cation salt thereof;

(3) $COC_nH_{2n}CO_2H$ wherein n is 1 to 6, or a cation salt thereof;

(4) $CONAC_nH_{2n}CO_2H$ wherein A is as defined in (1), n is 1 to 6, or a cation salt thereof;

(5) $COOC_nH_{2n}CO_2H$ wherein n is 1 to 6, or a cation salt thereof;

(6) $CONA(CHB)CO_2H$ wherein A is as defined in (1) and B is a residue of an amino acid, or a cation salt thereof;

(7) $COCHBNR_1R_2$ wherein B is a residue of an amino acid, $R_1$ and $R_2$ independently are H, $C_1$-$C_6$ alkyl, and phenyl, or an acid addition salt thereof;

(8) $CONAC_nH_{2n}NR_1R_2$ wherein A is as defined in (1), $R_1$ and $R_2$ independently are as defined in (7), n is 2 to 6, and acid addition salts thereof;

(9) $COOC_nH_{2n}NR_1R_2$ wherein $R_1$ and $R_2$ independently are as defined in (7), n is 2 to 6, and acid addition salts thereof;

(10) $COC_nH_{2n}NR_1R_2$ wherein $R_1$ and $R_2$ independently are as defined in (7), n is 1 to 7 and acid addition salts thereof; and

(11) COX where X is a leaving group;

The preferred group for R is

or a cation salt thereof.

By "cation salt" in (1)–(6) above is meant a salt of Li, K, Mg, Na, Ca, ($C_1$-$C_4$alkyl)ammonium.

By "acid addition salt" is meant pharmaceutically acceptable salts such as hydrochloride, hydrobromide, maleate, citrate, tartrate, acetate, succinate and the like.

The amino acids contributing to "B" above include serine, homoserine, ornithine, arginine, histidine, homocysteine, alanine, leucine, isoleucine lysine, methionine, phenylalanine, threonine, valine, glutamine, glycine, phenylalanine, tryptophan and the like.

By a "leaving group" is meant a group which departs with an electron pair. Representative leaving groups are chloride, bromide, iodide and anhydrides of protonated carboxylic acids, sulfonic acids, imidazoles and strongly acidic phenols.

By "neutral pH" is meant pH 6-8.

In referring to compounds hereinafter, the designation "A" following the word "Compound" will refer to a compound of formula (A) and the designations "1", "2", "3" and "4" will indicate the nucleus. Thus, "Compound A-1" will refer to a compound in which U, V and W are all hydroxy; "Compound A-2" to a compound in which U and W are H and V is OH; "Compound A-3" to a compound in which U and V are H and W is OH; and "Compound A-4" to a compound in which U is H and V and W are OH. R' and R will be designated by radical names following the number designation.

Preferred compounds are those in which (1) U and W are both OH, (2) U and W are both H, and (3) U and V are H and W is OH, in which R' is 9,11-dimethyltridecyl (DMTD), and R is phosphate (Phos) and which may be represented by the following formulas A-1a, A-2a, A-3a respectively. A-1a (=A-1-DMTD-Phos), A-2a (=A-2-DMTD-Phos) and A-3a (=A-3-DMTP-Phos).

The compounds may be identified as (1) Compound A-1(DMTD-Phos), (2) Compound A-2(DMTD-Phos), and (3) Compound A-3 (DMTD-Phos).

The compounds of the present invention have antifungal and antiprotozoal activity. As antifungal agents, they are useful for the control of both filamentous fungi and yeasts. Among the filamentous fungi which may be controlled are Aspergillus species such as *Aspergillus flavus, Aspergillus fumigatus*, Neurospora species, Fusarium species, Alternaria species, and *Cochliobolus miyabeanus* and the like. They are also useful for the treatment of mycotic infections, especially those caused by the Candida organisms such as *C. albicans, C. parapsilosis* and the like. As antiprotozoal agents they may be useful for the control of organisms causing amebiasis such as *Entamoeba histolytica*, or malaria such as Plasmodium species, or other organisms such as Trypanosoma species, Toxaplasma species, Cryptosporidia and the like. They are especially useful for the prevention

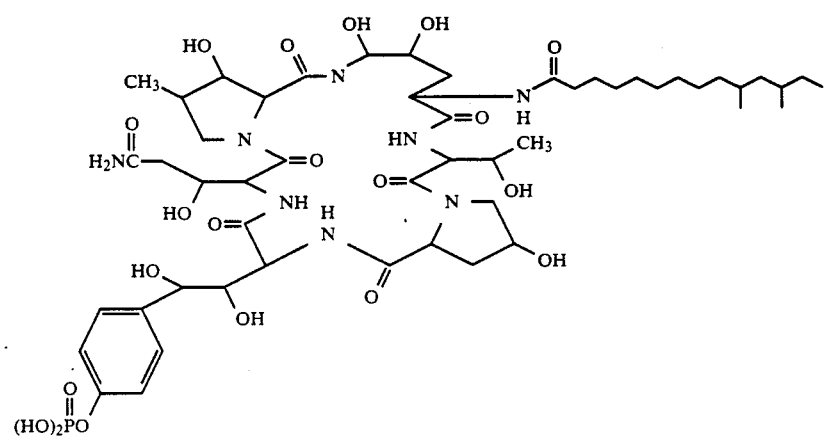

A-1(DMTD-Phos)

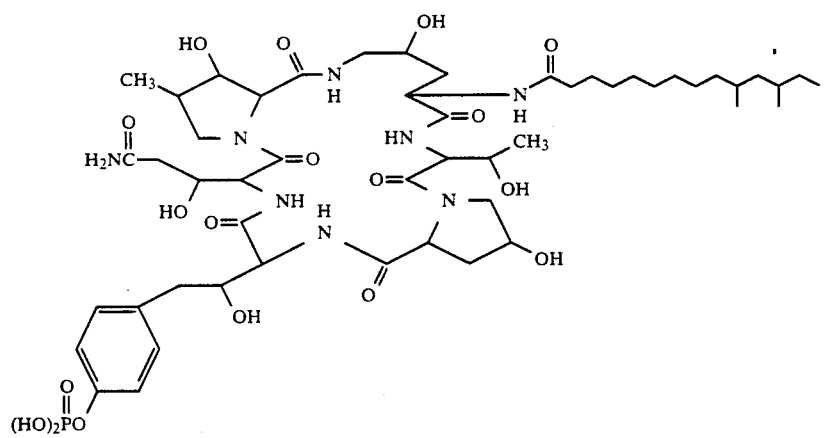

A-2(DMTD-Phos)

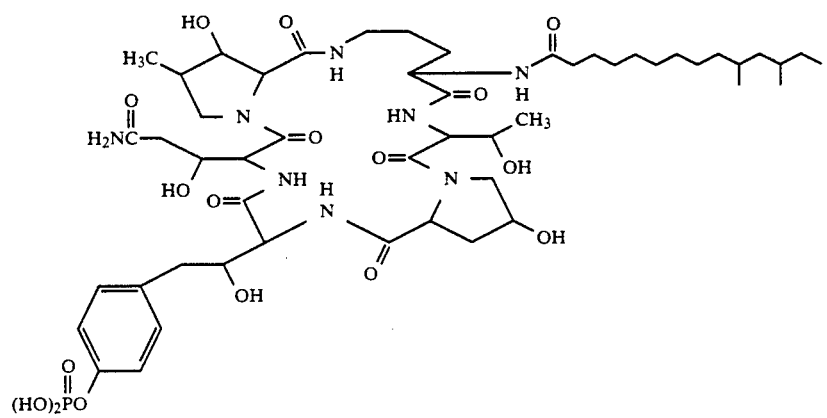

A-3(DMTD-Phos)

and or treatment of *Pneumocystis carinii* infections to which immune compromised patients are especially susceptible.

The compounds of the present invention which are generally white or light colored solids are derivatives of antibiotic lipopeptides. Unlike the parent compounds, the present compounds have good solubility properties in water and aqueous media. This property renders the compounds of the present invention more useful as therapeutic agents than the parent compound in many applications. Thus, they are adaptable to being used more readily in injectible compositions. Moreover, the compounds may have a prolonged duration of action.

The compounds of the present invention may be prepared from a lipopeptide having the formula (Z) by acylating at the phenolic hydroxyl and forming an ester link. The lipopeptide having formula Z are natural occurring or semi-synthetic lipopeptides obtained as subsequently described. The overall result may be represented by the following equation:

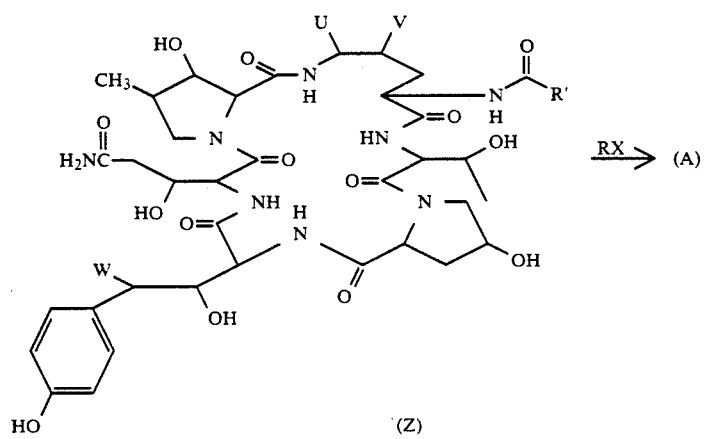

(Z)

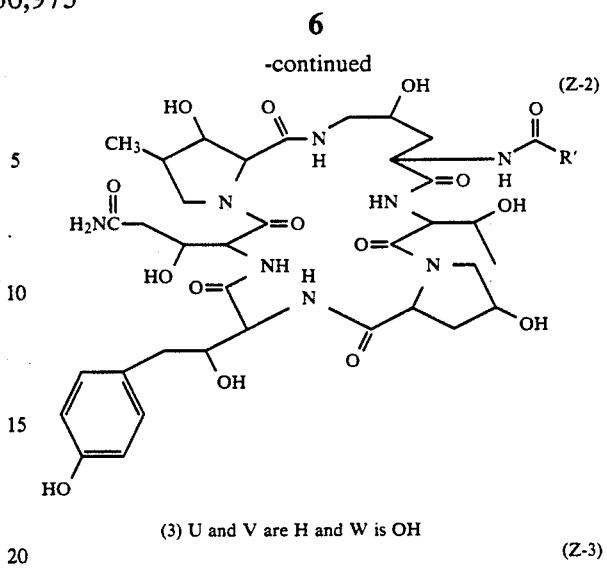

(3) U and V are H and W is OH (Z-2)

(Z-3)

The individual nuclei for the lipopeptide starting material may be seen in the following formulas:

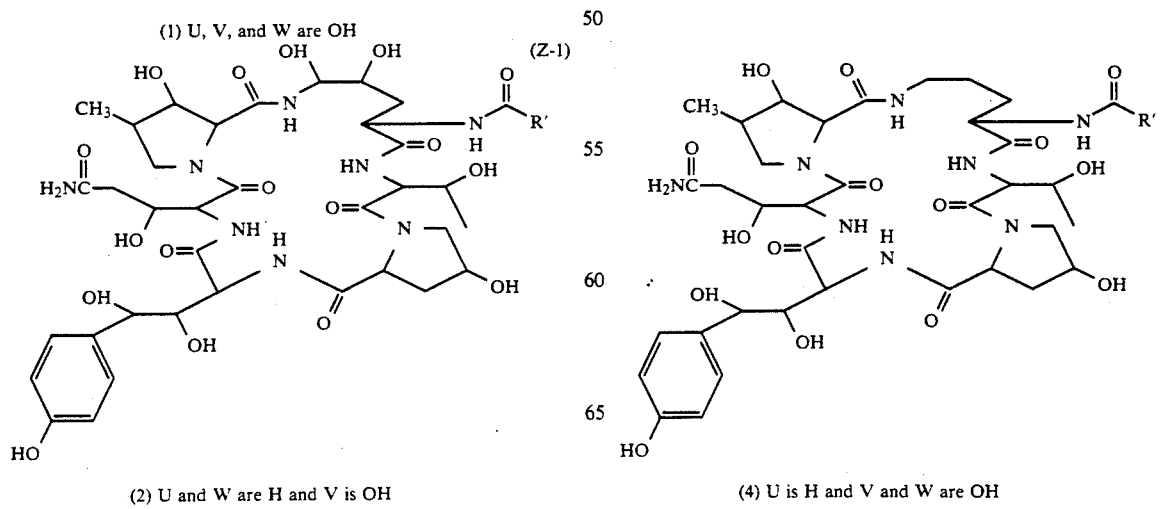

(1) U, V, and W are OH (Z-1)

(2) U and W are H and V is OH (4) U is H and V and W are OH

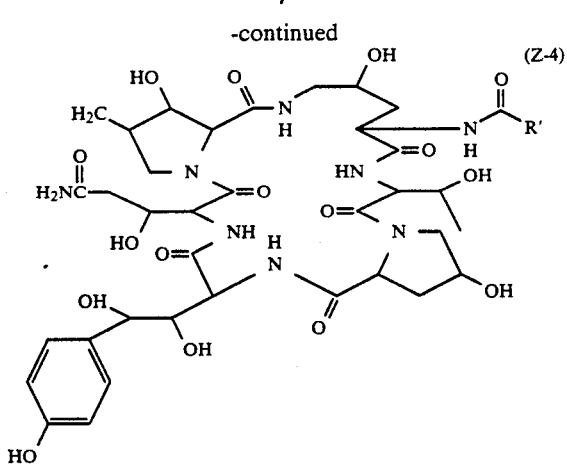
(Z-4)

Since the acyl group must have an ionizable group after completion of the acylation, the ionizable group is preferably protected during the acylation and the protecting group removed after completion of the acylation. Moreover, if U is hydroxyl, e.g., formula Z-1, it also may be protected during the acylation. Thus, the preparation of the desired products of the present invention may entail at least one protection/deprotection.

When U in formula (Z) is hydrogen, as in formula Z-2, Z-3 or Z-4, the compound may be acylated directly. When U in Formula Z is hydroxyl, as in nucleus Z-1 the first step is the etherification of the compound to form an ether, according to the following equation:

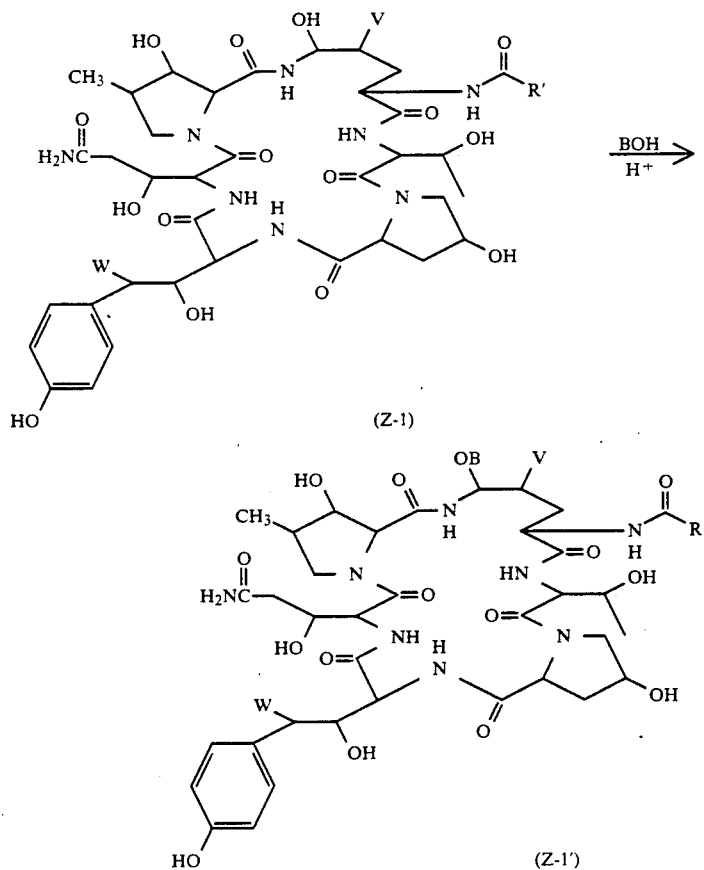

BOH is conveniently benzyl alcohol although other ether forming and readily cleavable alcohols may be employed, such as p-methoxybenzyl alcohol and 2,2,2-trichloroethanol.

The ether formation may be carried out by adding benzyl alcohol and p-toluenesulfonic acid to a solution or dispersion of the lipopeptide in a solvent and stirring at room temperature for from about 16 to 26 hours. The volatiles are then removed in vacuo and the ether product intermediate obtained as residue. The latter may be purified by preparative high performance liquid chromatography (HPLC). The resulting benzyl ether may be employed in the acylation.

The benzyl ether of a Z-1 lipopeptide or a Z-2, Z-3 or Z-4 lipopeptide is then acylated. The acylation may be carried out by first adding dropwise with stirring at room temperature under an atmosphere of nitrogen, a 1M hexane solution of lithium hexamethyldisilazide (Aldrich) to a pyridine solution of the appropriate lipopeptide or benzyl ether of a lipopeptide and the resulting mixture stirred for 10 to 15 minutes. Then, a solution of RX is added quickly and the resulting mixture stirred from 15 to 60 minutes to obtain the R ester of the lipopeptide or of the benzyl ether of the lipopeptide. The volatiles are then removed in vacuo to obtain the crude ester as a residue. The latter is then purified by preparative high performance liquid chromatography (HPLC) using $H_2O/CH_3CN$ as eluting agent. The eluant fractions having the desired retention time are lyophilized to obtain the desired intermediate ester.

The RX may by any of the compounds which would be embraced in the formula using the aforecited definitions for R and for X.

The preferred derivatives of the lipopeptides are phosphate esters. When the ester is a phosphate ester, the preferred esterification intermediate is a dibenzyl phosphate ester. The dibenzyl phosphate ester may be prepared by adding a solution of tetrabenzylpyrophosphate in pyridine to a stirred mixture of lipopeptide or benzyl ether of lipopeptide and lithium hexamethyldisilazide to obtain the dibenzylphosphate ester of the lipopeptide.

The acid or acid salt of the ester may be obtained by low pressure hydrogenolysis of the dibenzylphosphate ester of the lipopeptide or benzyl ether of the lipopeptide. During hydrogenolysis both the benzyl of the phosphate ester an the benzyl of the benzyl ether are cleaved to obtain a phosphate ester of the lipopeptide.

If it is desired to obtain the ultimate ester as its water-soluble salt, the hydrogenolysis may be carried out under mildly alkaline conditions and the desired product recovered as its salt. The free acid may be obtained by controlled acidification.

In one preferred method of carrying out the hydrogenolysis, a solution of dibenzylphosphate in aqueous ethanol is hydrogenated at 1 atmosphere over Pd-C catalyst for 10 to 20 hours whereupon the benzyl groups the phosphate ester are removed to obtain Compound I as an acid. If the starting lipopeptide is benzyl ether, the benzyl of the ether is also removed. When it is desired to obtain the ultimate ester product as a salt of the acid, the hydrogenolysis medium may be made mildly alkaline with alkali metal bicarbonate and the salt recovered directly. Alternatively, the free acid may be recovered on hydrogenolysis and subsequently converted to the salt by methods known in the art.

When R is a sulfonic acid ester or carboxylic acid ester, the reaction may be carried out in a manner similar to that described for the phosphoric acid ester. R may also be a radical in which the charged group at a neutral pH is an ammonium group formed preferably from the amino group of an amino acid which has been esterified at the phenolic hydroxyl.

In certain instances the preferred R may be a sulfate ester as described in specification (2). In these cases the sulfate ester may be prepared directly by treatment of a solution of the lipopeptide or lipopeptide benzyl ether in pyridine with sulfur trioxide pyridine complex to produce the pyridinium sulfate ester. If the free acid is desired it may be obtained by acidification with a strong acid such as hydrochloric acid followed by purification using a "Zorbax" C8 reverse phase HPLC column as stationary phase. If the lipopeptide benzyl ether is employed the benzyl ether may be removed by hydrogenolysis as described above.

When RX is a carboxylic acid derivative the preferred reagents for acylation are the carboxylic acid chlorides and anhydrides. The incipient charged group if it is to be a carboxylic acid salt may preferably be protected during the acylation reaction as a benzyl ester or other easily removed esters such as 2,2,2-trichloroethyl esters or allyl esters. If the incipient charged group is to be an ammonium species, the amine is conveniently protected during the acylation procedure as its benzyloxycarbonyl derivative. Other protecting groups for the ammonium group may include t-butoxycarbonyl or 2,2,2-trichloroethoxycarbonyl or other protecting groups well known to those skilled in the art. Thus, in one preferred esterification, the lipopeptide or lipopeptide benzyl ether in pyridine containing 4-dimethylaminopyridine as catalyst is treated with the symmetrical anhydride of the carboxylic acid to produce the carboxylic ester. Deprotection preferably by hydrogenolysis of the benzyl ester, if the charged group is to be an acid, or by hydrogenolysis of the benzyloxycarbonyl group, if the charged group is to be an amine, then releases carboxylic acid or amine respectively. If the charged group is to be an acid then the hydrogenolysis may be carried out under mildly alkaline conditions to obtain the water soluble salt directly. Conversely if the charged group is to be amine base the hydrogenolysis may be carried out under mildly acidic conditions to obtain the water soluble ammonium salt directly.

It certain instances such as in specifications (4), (6), and (8) above the ester linkage forms a portion of a carbamate. In those cases where A as defined in specification (1) above is hydrogen, the preferred reagent for acylation is the isocyanate. The incipient charged group if it is to be a carboxylic acid salt preferably may be protected during the acylation reaction as a benzyl ester or other easily removed esters such as 2,2,2-trichloroethyl esters or allyl esters. If the incipient charged group is to be an ammonium species, the amine is conveniently protected during the acylation procedure as its benzyloxycarbonyl derivative. Other protecting groups for the ammonium group may include t-butoxycarbonyl or 2,2,2-trichloroethoxycarbonyl or other protecting groups well known to those skilled in the art. Thus in a preferred esterification, the lipopeptide or lipopeptide benzyl ether in pyridine containing 4-dimethylaminopyridine is treated with the isocyanate to produce the carbamate. Deprotection may then proceed in a preferred case by hydrogenolysis as described above to release the charged group. In those instances in which A is other than hydrogen as defined in specification (1) above, a different procedure must be used. In these cases a preferred method involves initial formation of a reactive carbonate. Thus a solution of the lipopeptide or lipopeptide benzyl ether in pyridine containing 4-dimethylaminopyridine is treated with p-nitrophenylchloroformate and in this way the mixed p-nitrophenylcarbonate is prepared. In a separate step the p-nitrophenylcarbonate is converted to the desired carbamate. Treatment of the p-nitrophenylcarbonate in dimethylformamide with a secondary amine provides the protected carbamate. Deprotection may then proceed in a preferred case by hydrogenolysis as described above to unveil the charged group and provide the compounds described in specification (4), (6) and (8) above where A is other than hydrogen.

When compounds such as those described in specifications (5) and (9) above are desired the ester link forms a portion of a carbonate. In these cases the preferred reagents for acylation are the chloroformates. The incipient charged group if it is to be a carboxylic acid salt preferably may be protected during the acylation reaction as a benzyl ester or other easily removed esters such as 2,2,2-tricholorethyl esters or allyl esters. If the incipient charged group is to be an ammonium species, the amine is conveniently protected during the acylation procedure as its benzyloxycarbonyl derivative. Other protecting groups for the ammonium group may include t-butoxycarbonyl or 2,2,2-trichloroethoxycarbonyl or other protecting groups well known to those skilled in the art. Thus, in a preferred esterification, the lipopeptide or lipopeptide benzyl ether in pyridine containing 4-dimethylaminopyridine is treated with the chloroformate to produce the carbonate. Deprotection may then proceed in a preferred case by hydrogenolysis as described above to release the charged group.

The compounds of the present invention are useful for inhibiting or alleviating *Pneumocystis carinii* infections. In such use, Compound I or a composition containing Compound I is administered in a therapeutically effective or inhibitory amount to subjects infected with or susceptible to being infected with *Pneumocystis carinii*.

The efficacy of the compounds of the present invention for therapeutic or anti-infective purposes may be demonstrated in studies on immunosuppressed rats.

In a representative study, the effectiveness of Compound A-2a was determined. Sprague-Dawley rats (weighing approximately 250 grams) were immuno-suppressed with dexasone in the drinking water (2.0 mg/L) and maintained on a low protein diet for five weeds to induce the development of pneumocystis pneumonia from a latent infection. Before drug treatment, two rats were sacrificed to confirm the presence of *Pneumocystis carinii* pneumonia (PCP); both rats were found to have infections. Six rats (weighing approximately 150 grams) were injected twice daily for four days intraperitoneally (I.P.) with Compound A-2a in 0.25 ml of vehicle (distilled water). A vehicle control was also carried out. All animals continued to receive dexasone in the drinking water and low protein diet during the treatment period. At the completion of the treatment, all animals were sacrificed, the lungs were removed and processed, and the extent of disease determined by microscopic analysis of stained slides. The results of this study showed Compound A-2a was effective in eliminating *P. carinii* cysts in four days with an $ED_{90}$ of approximately 2 mg/kg.

In a similar experiment, the animals were sacrificed, the lungs removed and processed, and the extent of disease determined by microscopic analysis of stained slides. The results showed that Compound A-3a was effective at eliminating *P. carinii* cysts in four days with an $ED_{90}$ of approximately 2.5 mg/kg.

The compounds of the present invention are active against many fungi and particularly against Candida species. The antifungal properties may be illustrated with the minimum fungicidal concentration (MFC) determinations against certain Candida organisms in a microbroth dilution assay carried out in a Yeast Nitrogen Base (Difco) medium with 1% dextrose (YNBD). In carrying out the assay, Compound A-2a and A-3a were solubilized in 10% dimethyl sulfoxide (DMSO) and diluted to 2560 $\mu g/ml$. The compounds were then diluted to 256 $\mu g/ml$ in YNBD. 0.15 $\mu l$ of the suspension was dispensed to the top row of a 96-well plate (each well containing 0.15 ml of YNDB) resulting in a drug concentration of 128 $\mu g/ml$. Two-fold dilutions were then made from the top row to obtain final drug concentrations ranging from 128 to 0.06 $\mu g/ml$.

The yeast cultures, maintained on Sabouraud dextrose agar were transferred to YM broth (Difco) and incubated overnight at 35° C. with shaking (250 rpm). After incubation, each culture was diluted in sterile water to yield a final concentration of $1-5 \times 10^6$ colony forming units (CFU)/ml.

96-well microplates were inoculated using a MIC-2000 (Dynatech) which delivers 1.5 $\mu l$ per well yielding a final inoculum per well of $1.5-7.5 \times 10^3$ cells. The microplates were incubated at 35° C. for 24 hours. The minimum inhibitory concentrations (MICs) were recorded as the lowest concentrations of drug showing no visible growth.

After recording the MIC, the plates were shaken to resuspend the cells. Thereafter, 1.5 ml samples from the wells in the 96-well microplate were transferred to a single well tray containing Sabouraud dextrose agar. The inoculated trays were incubated 24 hours at 28° C. and then read. The MFC is defined as the lowest concentration of drug showing no growth or less than 4 colonies per spot. The results are seen in the following table:

| Fungi Strain No. | Minimum Fungicidal Concentration ($\mu g/ml$) | |
|---|---|---|
| | A-2a | A3-a |
| *C. albicans* | | |
| MY 1055 | 1 | 2 |
| MY 1208 | 1 | 4 |
| MY 1028 | 1 | 4 |
| *C. tropicalis* | | |
| MY 1012 | 0.5 | 1 |
| *C. parapsilosis* | | |
| MY 1010 | 16 | >128 |

The outstanding properties are most effectively utilized when the compound is formulated into novel pharmeceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1% by weight of Compound A or one of the components. Concentrate compositions suitable for dilutions prior to use may contain 90% or more by weight. The compositions include compositions suitable for rectal, topical, parenteral (including subcutaneous, intramuscular, and intravenous), pulmonary (nasal or buccal inhalation), nasal administration, or insufflation. The compositions may be prepacked by intimately mixing Compound A with the components suitable for the medium desired.

When the compound is for antifungal use any method of administration may be used. For treating mycotic infection oral administration is frequently preferred. When oral administration is to be employed, it may be with a liquid composition or a solid composition. For liquid preparations, the therapeutic agent is formulated with liquid carriers such as water, glycols, oils, alcohols, and the like, and for solid preparations such as capsules and tablets, solid carriers such as starches, sugars, kaolin, ethyl cellulose, calcium and sodium carbonate, calcium phosphate, kaolin, talc, lactose, generally with lubricant such as calcium stearate, together with binders, disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Composition in unit dosage form constitutes an aspect of the present invention.

The Compound A also may be formulated in therapeutic compositions for intravenous or intraperitoneal injection and may be presented in unit dosage form in ampoules or in multidose containers, if necessary with an added preservative. The compositions may also take such forms as suspensions, solutions or emulsions in oily or aqueous vehicles such as 0.85 percent sodium chloride or 5 percent dextrose in water, and may contain formulating agents such as suspending stabilizing and/or dispersing agents. Buffering agents as well as additives such as saline or glucose may be added to make the solutions isotonic. The drug also may be solubilized in alcohol/propylene glycol or polyethyleneglycol for drip intravenous administration. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is to be employed for control of pneumocystis infections it is desirable to directly treat lung and bronchi. For this reason, inhalation methods are preferred. For administration by inhalation, the compounds of the present invention are conveniently delivered in the form of an aerosol spray presentation from pressurized packs of nebulisers. The preferred delivery system for inhalation is a metered dose inhalation (MDI) aerosol, which may be formulated as a suspension or solution of Compound A in suitable propellants, such as fluorocarbons or hydrocarbons.

Although the compounds of the present invention may be employed as tablets, capsules, topical compositions, insufflation powders, suppositories and the like, the advantage of the derivatives of the present invention over the parent lipopeptide is in their water solubility. Hence, the compounds of the present invention are most effectively utilized in injectible formulations and also in liquid compositions suitable for aerosol sprays.

Compound A also may be employed against a broad spectrum of yeasts and filamentous fungi (molds). For non-medical application, the product of the present invention, may be employed in compositions in an inert-carrier which includes finely divided dry or liquid diluents, extenders, fillers, conditioners and excipients, including various clays, diatomaceous earth, talc, and the like, various organic liquids such as lower alkanols, for example, ethanol and isopropanol, or kerosene, benzene, toluene and other petroleum distillate fractions or mixtures thereof. However, as with medical applications, the compounds are best utilized in aqueous compositions.

The following examples illustrate the invention but are not to be construed as limiting:

EXAMPLE I

1-[4-hydroxy-N2-(10,12-dimethyl-1-oxotetradecyl)-ornithine]-4-[3-hydroxy-4'-O-phosphoryl-homotyrosine]-5-[3-hydroxyglutamine]echinocandin B.

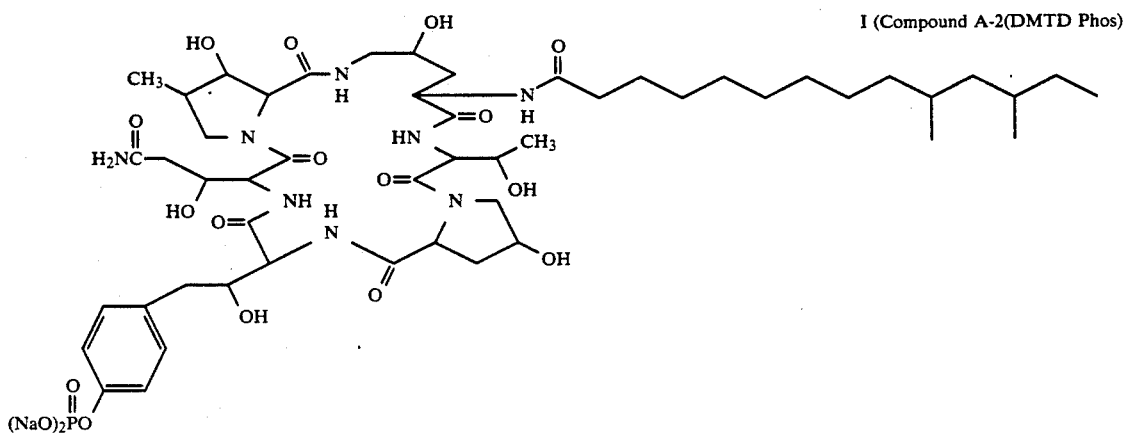

I (Compound A-2(DMTD Phos)

Part A. Dibenzylphosphate Ester Formation 0.172 milliliter (0.172 mmol) of lithium hexamethyldisilazide (1M in hexane, Aldrich) was added dropwise with stirring under nitrogen atmosphere to a solution of 150 milligrams (0.143 mmol) of Z-2 (DMTD) in 1 milliliter of dry pyridine and stirring continued after completion of the addition for about 10 minutes. Then, a solution of 93 milligrams (0.172 mmol) of tetrabenzyl pyrophosphate in 0.5 milliliter of pyridine was added quickly whereupon a yellow solution was obtained. The mixture was stirred for 1 hour; then the volatiles were removed in vacuo. The residue was purified by preparative high performance liquid chromatography (HPLC) (21.2×250 mm. C8 "Zorbax") eluting with water/acetonitrile the appropriate fractions (as determined by UV at 210 nm) (40/60) and of the eluate were combined and lyophilized to obtain 69 milligrams (37 percent) of the dibenzyl phosphate ester as a white powder.

Part B. Hydrogenolysis of Dibenzyl phosphate 68 milligrams (0.0521 mmol) of the dibenzyl phosphate obtained in Part A was dissolved in 3 milliliters of absolute ethanol. To it was added a solution of 8.8 milligrams (0.104 mmol) of sodium bicarbonate in 3 milliliters of distilled water. Next, 50 milligrams of 10% Pd-C was added and the resulting mixture stirred under 1 atmosphere of hydrogen for 1.5 hours. The resulting mixture was filtered and concentrated in vacuo to obtain the desired product Compound A-2 (DMTD-Phos) as residue. The product was purified by preparative HPLC (9.2×250 mm C8 "Zorbax") eluting with water/acetonitrile (55/45) and the appropriate fractions as determined by UV at 210 nm were combined and lyophilized to obtain 53 milligrams (87 percent yield) of product as a white powder. The solubility in water of the powder was >40 mg/ml.

$^1$HNMR: (300 MHz, CD$_3$OD): δ7.21 (d, J=6 Hz,2H) and 7.13 (d, J=6 Hz,2H), 2.63(m).

Mass Spectrum: (FAB): 1127 (M+1)(free acid).

EXAMPLE II

1-[N2-(10,12-dimethyl-1-oxotetradecyl)-ornithine]-4-[3,4-dihydroxy-4'-O-phosphoryl-homotyrosine]-5-[3-hydroxyglutamine] echinocandin B.

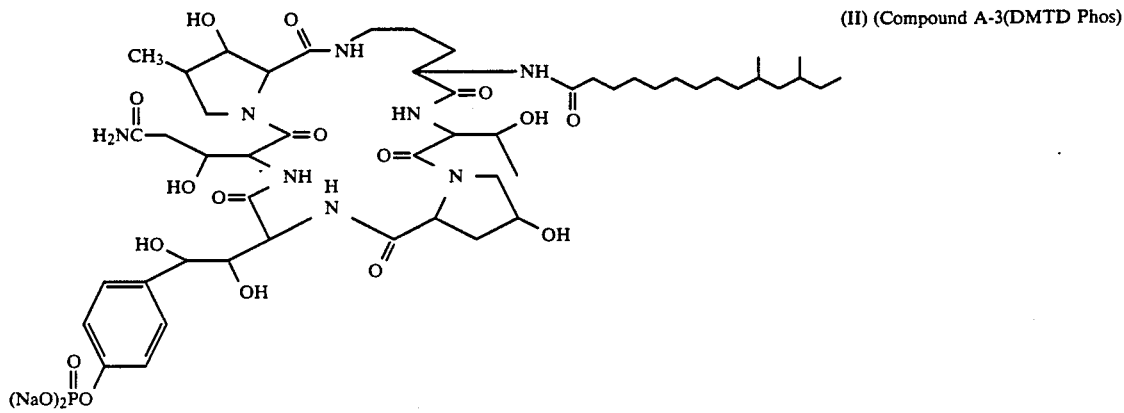

(II) (Compound A-3(DMTD Phos))

Part A. Dibenzylphosphate Ester Formation

To a solution of 250 milligrams (0.239 mmol) of Compound Z-3 (R'=DMTD) in 2 milliliters of dry pyridine under nitrogen atmosphere was added dropwise with stirring 0.287 milliliter (0.287 mmol) of lithium hexamethyldisilazide (1M in hexane, Aldrich) and stirring continued for ten minutes. A solution of 155 milligrams (0.287 mmol) of tetrabenzylpyrophosphate was added quickly whereupon the solution became yellow. The solution was stirred for one hour. At the end of this time, the volatiles were removed in vacuo and the residue was purified by preparative HPLC (21.2×250 mm C8 "Zorbax") using water/acetonitrile (40/60) as eluant. The fractions were monitored by UV at 210 nm and the appropriate fractions were combined and lyophilized to obtain 91 milligrams of the product as a white powder.

Part B. Hydrogenolysis of Dibenzyl phosphate 87 milligrams (0.0667 mmol) of the dibenzyl phosphate prepared in Part A was dissolved in 4 milliliters of absolute ethanol. To it was added a solution of 11.3 milligrams (0.133 mmol) of sodium bicarbonate in 4 milliliters of distilled water. Next, 64 milligrams of 10% Pd-C was added and the resulting mixture stirred under 1 atmosphere of hydrogen at room temperature for two hours. At the end of this period, the mixture was filtered and concentrated in vacuo and thereafter lyophilized to obtain 79.2 milligrams of A-3 (DMTD-Phos) as a white powder with a solubility >28 mg/ml.

$^1$NMR: (300 MHz, CD$_3$OD): $\delta$7.30 (d,J=9 Hz, 2H) and 7.24 (d, J=9 Hz,2H).

Mass Spectrum: (FAB): 1171 (M+1, disodium salt).

EXAMPLE III

1-[4,5-dihydroxy-N2-(10,12-dimethyl-1-oxotetradecyl)-ornithine-4-[3,4-dihydroxy-4'-O-phosphoryl-homotyrosine]-5-[3-hydroxyglutamine]echinocandin B disodium salt (III)

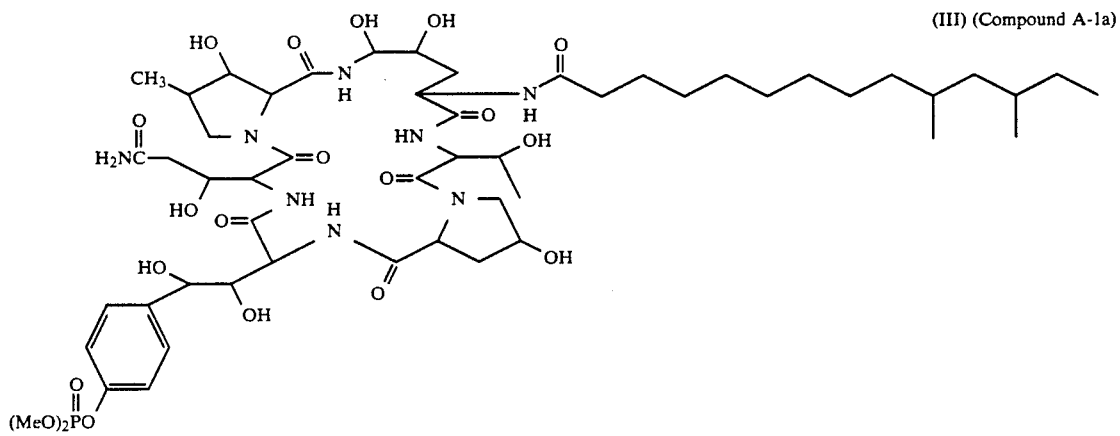

(III) (Compound A-1a)

Part A. Benzyl Ether

1-[4-hydroxy-5-benzyloxy-N2-(10,12-dimethyl-1-oxotetradecyl)-ornithine-5[3-hydroxyglutamine]echinocandin B (IIIa)

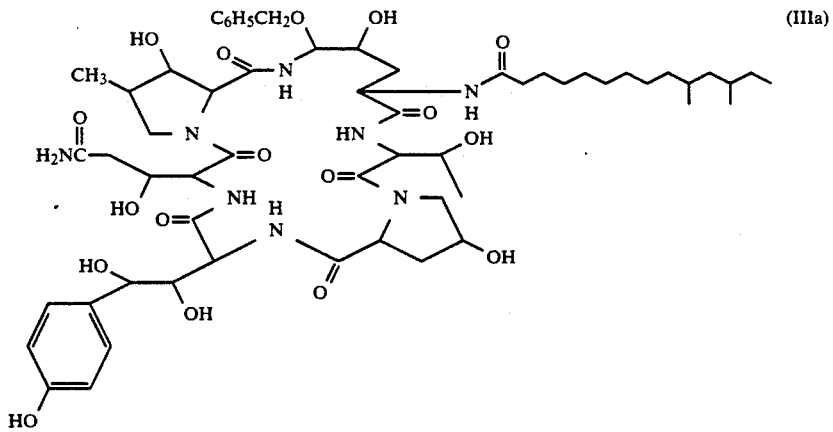

350 mg of 1-[4,5-dihydroxy-N2-(10,12-dimethyl-1-oxotetradecyl)-ornithine]-5-(3-hydroxyglutamine)echinocandin B (Compound Z-1(DMTD)) is suspended in 7 milliliters of tetrahydrofuran and to the suspension is added 0.68 milliliter of benzyl alcohol and 7 milligrams of p-toleuenesulfonic acid. 3 milliliters of dimethylformamide is added and the resulting solution stirred for 24 hours at room temperature. At the end of this period, the volatiles are removed in vacuo to obtain a residue which is purified by preparative HPLC (21.2×250 mm C8 "Zorbax" (DuPont)) eluting with water/acetonitrile (40/60) at 10 ml/min. and collecting 15 milliliter fractions. The appropriate fractions (as determined by UV at 210 nm) are combined and lyophilized to obtain the benzyl ether intermediate (IIIa), molecular weight of 1168.

Part B. Dibenzylphosphate Ester

1-[4-hydroxy-5-benzyloxy-N2-(10,12-dimethyl-1-oxotetradecyl)-ornithine]-4-[3,4-dihydroxy-4'-O,O-dibenzyl-phosphoryl-homotyrosine]-5-[3-hydroxyglutamine]echinocandin B (IIIb)

added quickly and the resulting solution stirred for 15 minutes. Then, the volatiles are removed in vacuo to obtain a residue. The residue is purified by preparative HPLC (9.4×250 mm C8 "Zorbax"), eluting with water/acetonitrile and collecting fractions. The appropriate fractions (as determined by UV at 210 nm) are lyophilized to obtain the desired dibenzyl phosphate intermediate (Ib) as a white solid, molecular weight of 1428.

Part C. Preparation of Sodium Salt Phosphate Ester (Hydrogenolysis of Dibenzylphosphate)

62 milligrams (0.0438 mmole) of the intermediate (Ib) above obtained is dissolved in 6 milliliters of water/ethanol (1:1) and to it is added a solution of 7.4 mg (0.0875 mmole) of sodium bicarbonate in distilled water. Next 60 milligrams of 10% Pd-C is added and the mixture stirred under 1 atmosphere of hydrogen at room temperature for 7 hours. The mixture is then filtered through a 0.2 micron filter, washed with 1:1 ethanol/water and concentrated on a rotary evaporator. The residue is on lyophilized to obtain the product as a white solid, molecular weight of 1196.

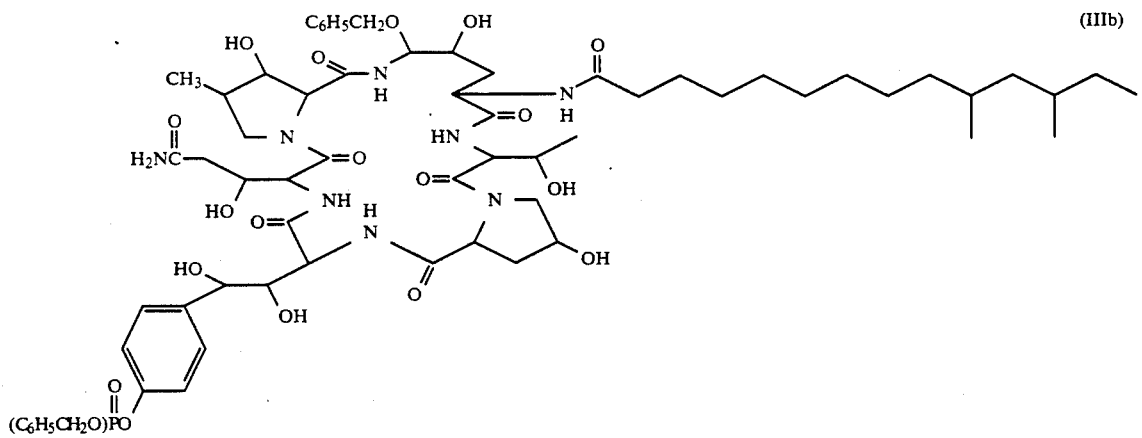

89 milligrams (0.076 mmole) of the benzyl ether of Z-1(DMTD) (formula Ia) is dissolved in 1.5 milliliters of dry pyridine under a nitrogen atmosphere. 152 microliters (0.152 mmole) of a 1M solution in hexane of lithium hexamethyldisilazide (Aldrich) is added dropwise and stirred for 10 minutes at room temperature. Then, a solution of 49 milligrams (0.0912 mmole) of tetrabenzylpyrophosphate in 0.5 milliliter of pyridine is

EXAMPLE IV

1-[4,5-dihydroxy-N2-(10,12-dimethyl-1-oxotetradecyl)-ornithine]-4-[3,4-dihydroxy-4'-O-(2-N-methylcarbamoylacetic acid)-homotyrosine]-5-[3-hydroxyglutamine]echinocandin B (IV)

temperature for 20 hours. At the end of this period, the mixture is concentrated in vacuo and the residue dissolved in water/acetonitrile and thereafter purified by preparative reverse phase chromatography, eluting with water/acetonitrile. The fractions containing the desired product are concentrated in vacuo to remove the acetonitrile and then lyophilized to obtain purified

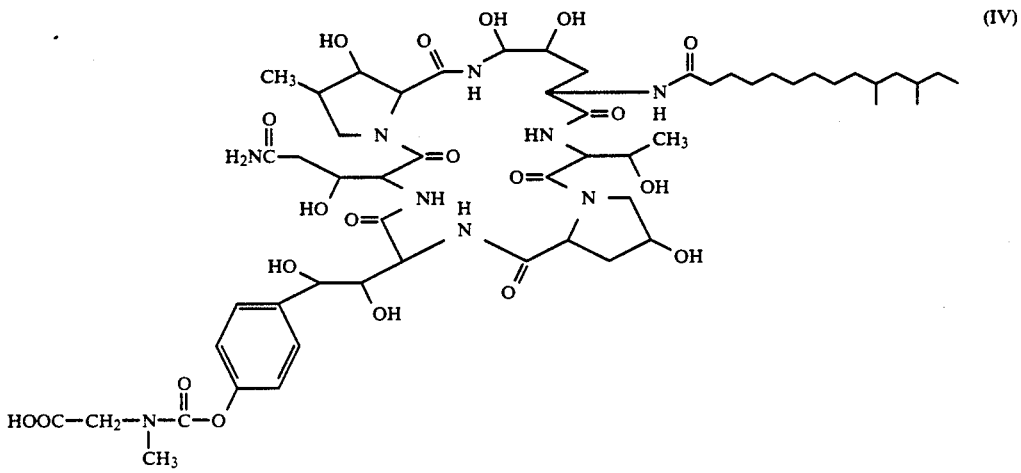

(IV)

Part A. Benzyl Ether

In a manner similar to that described in Example III, 0.68 ml of benzyl alcohol and 7 mg of p-toluenesulfonic acid are added to a solution of 350 mg of Compound Z-1(DMTD) in a mixture of 7 ml of tetrahydrofuran and 3 ml of dimethylformamide and the mixture stirred at room temperature for 24 hours. At the end the volatiles are removed in vacuo to obtain a residue which is purified on a preparative HPLC column using water/acetonitrile as eluant. The appropriate fractions are combined and lyophilized to obtain benzyl ether of Z-1(DMTD), molecular weight of 1168.

Part B.

1-[4-hydroxy-5-benzyloxy-N2-(10,12-dimethyl-1-oxotetradecyl)-ornithine]-4-[3,4-dihydroxy-4'-O-p-nitrophenylcarbonate-homotyrosine]-5-[3-hydroxyglutamine]echinocandin B p-nitrophenyl carbonate ester. Molecular weight is 1333.

Part C. 1-[4,5-dihydroxy-N2-(10,12-dimethyl-1-oxotetradecyl)-ornithine]-4-[3,4-dihydroxy-4'-O-(2-N-methylcarbamoylacetic acid)-homotyrosine]-5-[3-hydroxyglutamine]echinocandin B To a solution of 108 mg (0.081 mmol) of the p-nitrophenyl carbonate prepared as described in Part B in 1 ml of dry dimethylformamide is added 15 mg (1.1 eq) of benzyl sarcosine and the mixture allowed to stir at room temperature for 20 hours. The crude reaction mixture is concentrated in vacuo, the residue dissolved in water/acetonitrile and purified by reverse phase chromatography on "Zorbax" C8 column and eluted with acetonitrile/water. The fractions containing the desired intermediate is concentrated in vacuo to remove the acetonitrile and then lyophilized to obtain a purified

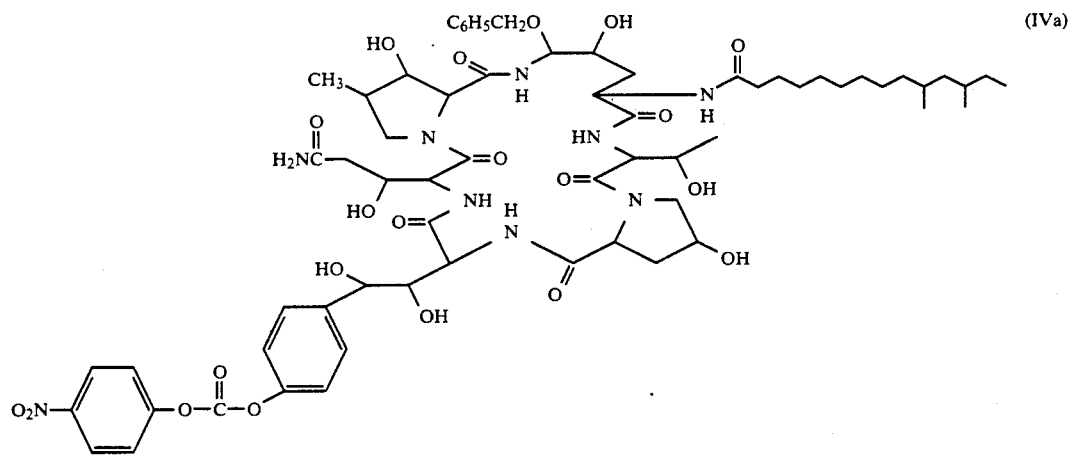

(IVa)

To a solution of the 0.273 (0.234 mmol) benzyl ether of Z-1(DMTD) prepared in Part A in 2.5 ml of dry pyridine is added sequentially 31 mg (1.1 eq) 4-dimethylaminopyridine and 52 mg (1.1 eq) of p-nitrophenylchloroformate and the mixture allowed to stir at room benzyl ester.

The ester is dissolved in 15 ml of absolute ethanol and to the solution is added 15 mg of 10% Pd-C and stirred at 1 atmosphere for 5 hours. At the end of this period, the mixture is filtered and the filtrate concentrated to obtain the desired product (III). The product is purified on preparative HPLC employing water/acetonitrile. The molecular weight is 1193.

EXAMPLE V

1-[4-hydroxy-N2-(10,12-dimethyl-1-oxotetradecyl)-ornithine]-4-[3-hydroxy-4'-O-(2-carbamoyl acetic acid)-homotyrosine]-5-[3-hydroxyglutamine]echinocandin B

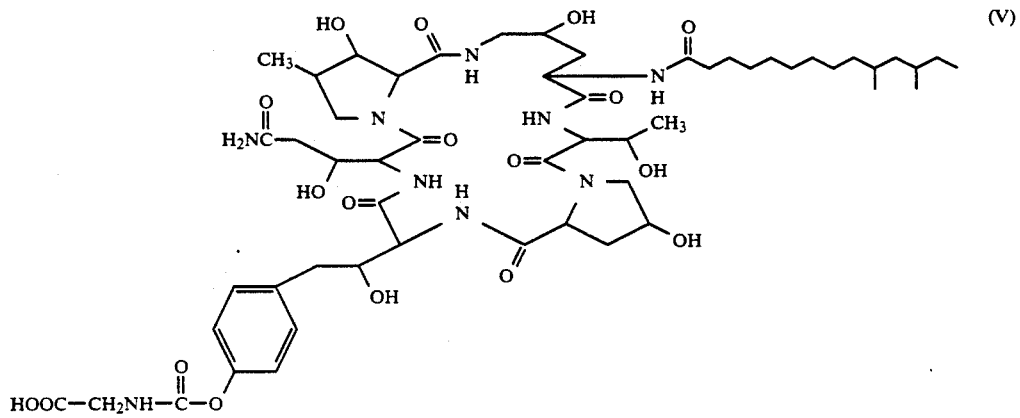

Part A.

1-[4-hydroxy-N2-(10,12-dimethyl-1-oxotetradecyl)-ornithine]-4-[3-hydroxy-4'-O-(benzyl 2-carbamoylacetate)-homotyrosine]-5-[3-hydroxyglutamine]echinocandin B)

To a solution of 28 milligrams (0.027 mmol) of Z-2 (DMTD) in 200 microliters of dry pyridine was added sequentially 5 milligrams (0.041 mmol) of 4-dimethylaminopyridine and 5.2 milligrams (1 eq) of benzyl 2-isocyanatoacetate in 100 microliters of pyridine and the mixture stirred at room temperature under nitrogen for one hour. The mixture is concentrated in vacuo and then dissolved in 25/75 acetonitrile/water. At this time HPLC assay showed only partial completion of reaction so another 5 milligrams of benzyl 2-isocyanatoacetate was added and stirred to obtain the desired product. The product was isolated by preparative HPLC using water/acetonitrile (30/70) as eluant at 10 ml/min and collecting 8 milliliter fractions to obtain the benzyl ester of compound of formula IV as a white solid.

Part B.

1-[4-hydroxy-N2-(10,12-dimethyl-1-oxotetradecyl)-ornithine]-4-[3-hydroxy-4'-O-(2-carbamoyl acetic acid)-homotyrosine]-5-[3-hydroxyglutamine]echinocandin B)

7 milligrams of the benzyl ester obtained in Part A was dissolved in 2.5 milliliters of 50/50 water/ethanol containing 0.50 milligrams of sodium bicarbonate. An equal weight of Pd-C was added and the reaction mixture was stirred at room temperature over 1 atmosphere of hydrogen for one hour. At the end of this time the mixture was filtered and the ethanol vaporized and the concentrate lyophilized to obtain the product of formula (IV). The compound has a molecular weight of 1147.

EXAMPLE VI

1-[4-hydroxy-N2-(10,12-dimethyl-1-oxotetradecyl)-ornithine-4-[3-hydroxy-4'-O-(malonic acid)-homotyrosine]-5-[3-hydroxyglutamine]echinocandin B

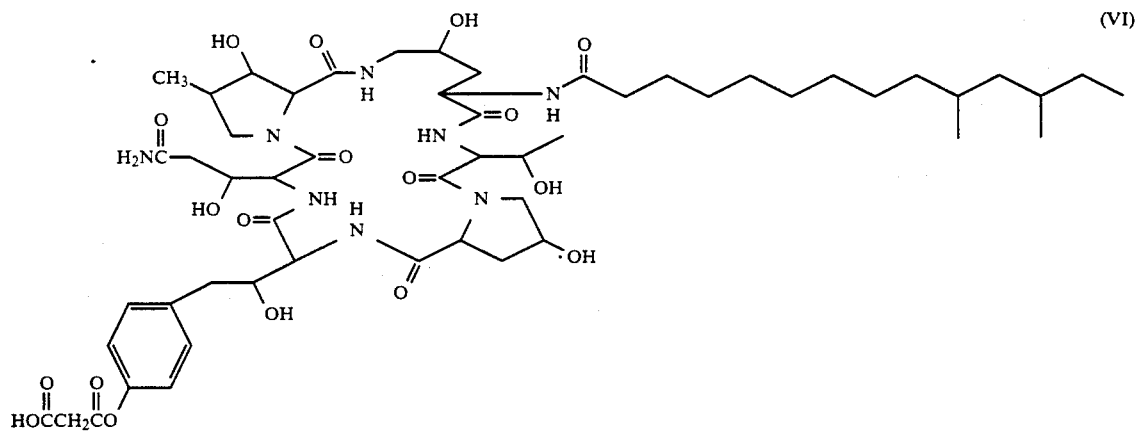

In reactions carried out in a manner similar to that described in the foregoing examples, 31 milligrams (1.1 eq) of 4-dimethylaminopyridine and 55 mg (1.1 eq) of monobenzyl malonic acid chloride are added sequentially to a solution of 250 milligrams (0.234 mmol) of Z-2(DMTD) in 2.5 ml of dry pyridine and the mixture stirred at room temperature. The reaction mixture is concentrated in vacuo, the residue dissolved in water-/acetonitrile and purified by preparative reverse phase chromatography. Fractions containing the desired material are concentrated in vacuo to remove the acetonitrile and then lyophilized to obtain the benzyl ester, 1-[4-hydroxy-N2-(10,12-dimethyl-1-oxotetradecyl)ornithine]-4-[3-hydroxy-4'-O-(benzylmalonate)-homotyrosine]-5-[3-hydroxyglutamine]echinocandin B.

The benzyl ester is then subjected to hydrogenolysis in ethanol over 10% palladium on carbon catalyst at room temperature for about 8 hours. Then the catalyst is filtered off and the filtrate concentrated to obtain 1-[4-hydroxy-N2-(10,12-dimethyl-1-oxotetradecyl)-ornithine]-4-[3-hydroxy-4'-O-(malonic acid)-homotyrosine]-5-[3-hydroxyglutamine]echinocandin B as residue. The latter is purified by reverse phase chromatography using water/acetonitrile. The compound has a molecular weight of 1132.

EXAMPLE VII

1-[4,5-dihydroxy-N2-(10,12-dimethyl-1-oxotetradecyl)ornithine-4-[3,4-dihydroxy-4'-O-(2-carbamoylacetic acid)-homotyrosine]-5-[3-hydroxyglutamine]echinocandin B To a solution of 273 mg (0.234 mmol) of the benzyl ether of Compound Z-1(DMTD) in 2.5 ml of dry pyridine is added sequentially 31 mg (1.1 eq) of 4-dimethylaminopyridine and 50 mg (1.1 eq) of benzyl-2-isocyanatoacetic acid and the resulting mixture stirred at room temperature for several hours. At the end of the this period, the mixture is concentrated in vacuo, taken up in water/acetonitrile and purified using reverse phase chromatography (1 inch diameter "Zorbax" C8 column) and eluted with water/acetonitrile. Fractions containing the desired material as determined by HPLC assay are concentrated in vacuo to remove acetonitrile and then lyophilized to obtain purified benzyl carbamate.

In a manner similar to that described in Examples I and II, 250 mg (0.2 mmole) of the benzyl carbamate of the benzyl ether of Z-1 (DMTD) is dissolved in 15 ml of absolute ethanol. Next, 200 mg of 10% Pd-C is added and the mixture stirred under 1 atmosphere of hydrogen

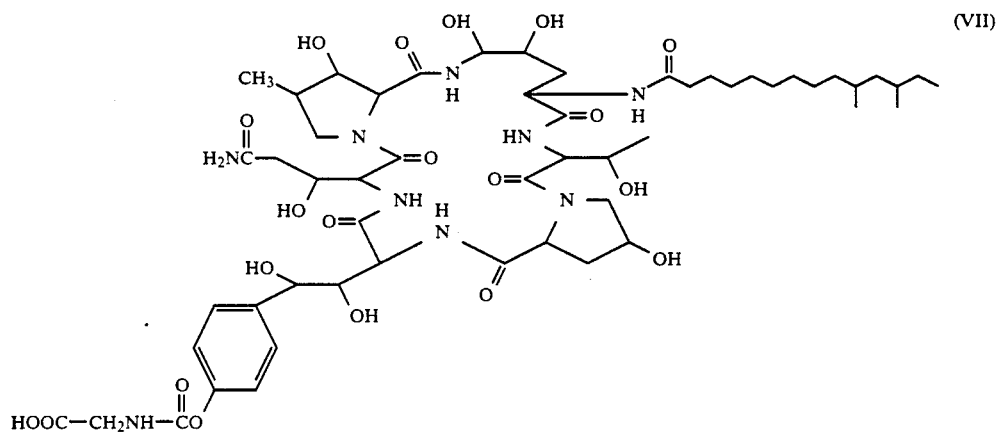

(VII)

In a manner similar to that described in Example III, 350 mg of Compound Z-1(DMTD) is suspended in 7 ml of tetrahydrofuran and to the suspension is added 0.68 ml of benzyl alcohol, 3 ml of dimethylformamide and 7 ml of p-toluenesulfonic acid and the resulting mixture stirred for 24 hours at room temperature. At the end of this period, the volatiles are removed in vacuo and the residue obtained purified by preparative HPLC using water/acetonitrile as eluant. The appropriate fractions are combined and lyophilized to obtain the benzyl ether, 1-[4-hydroxy-5-benzyloxy-N2-(10,12-dimethyl-1-oxotetradecyl)-ornithine]-4-[3,4-dihydroxyhomotyrosine]-5-[3-hydroxyglutamine]echinocandin B.

at room temperature for about 5 hours. The resulting mixture is then filtered, the filtrate concentrated to obtain the desired 1-[4,5-dihydroxy-N2-(10,12-dimethyl-1-oxotetradecyl)-ornithine]-4-[3-hydroxy-4'-O-(2-carbamoylacetic acid)-homotyrosine]-5-[3-hydroxyglutamine]echinocandin B as residue. The product is purified by reverse phase chromatography (1 inch diameter "Zorbax" C8 column) eluting with water/acetonitrile.

The compound has a molecular weight 1179.

EXAMPLE VIII

1-[4-hydroxy-N2-(10,12-dimethyl-1-oxotetradecyl)ornithine]-4-[3-hydroxy-4'-O-(glycyl)-homo-tyrosine]-5-[3-hydroxyglutamine]echinocandin B

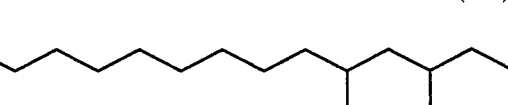

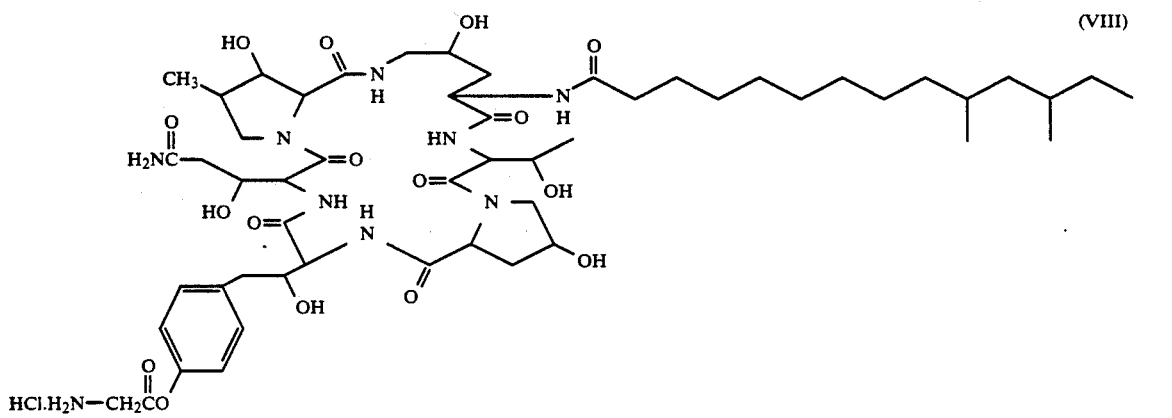

In a manner similar to that previously described, 31 milligrams (1.1 eq) of 4-diemethylaminopyridine and 126 milligrams (1.1 eq) of N-carboxybenzylglycine symmetrical anhydride are added sequentially to a solution 250 milligrams (0.234 mmol) of Z-2(DMTD) in 2.5 milliliters of dry pyridine and the mixture stirred at room temperature for 8 hours. It is then concentrated in vacuo, the residue dissolved in water/acetonitrile (40/60) and purified by preparative reverse phase chromatography, eluting with water/acetonitrile.

The fractions containing the desired material are combined and concentrated, and then lyophilized to obtain purified carboxybenzyl protected glycyl ester. 1-[4-hydroxy-N2-(10,12-dimethyl-1-oxotetradecyl)-ornithine]-4-[3-hydroxy-4'-O-(N-carboxybenzyl glycyl)-homotyrosine]-5-[3-hydroxyglutamine]echinocandin B.

The ester thus obtained is dissolved in 12 milliliters of ethanol containing an excess of anhydrous hydrochloric acid and 20 milligrams of 10% Pd-C catalyst is added and hydrogenation carried out at 1 atmosphere for 5 hours. At this time the catalyst is filtered off and the filtrate concentrated to recover. 1-[4-hydroxy-N2-(10,12-dimethyl-1-oxotetradecyl)ornithine-4-[3-hydroxy-4'-O-(glycyl)-homotyrosine]-5-[3-hydroxyglutamine]echinocandin B hydrochloride product. Molecular weight of the salt is 1139.5.

EXAMPLE IX

In similar operations, the following compounds are prepared:

| Compound No. | U | V | W | R | R'— |
|---|---|---|---|---|---|
| XI | OH | OH | OH | $SO_3H$ | DMTD |
| X | H | OH | OH | $O=P(ONa)_2$ | DMTD |
| XI | H | H | OH | $COCH_2COOH$ | $-C_{17}H_{35}n$ |
| XII | H | H | OH | $CONH(CH_2)_2COOH$ | |
| XIII | H | OH | OH | $CO(CH_2)_2NH_2 \cdot HCl$ | DMTD |
| XIV | H | OH | H | $CONH(CH_2)_2NH_2 \cdot HCl$ | $C_{13}H_{27}n$ |
| XV | H | OH | H | $O=P(OH)_2$ | $-(CH)_7CH=CH(CH_2)_5CH_3$ |
| XVI | H | OH | H | $COOCH_2COOH$ | $-C_{15}H_{31}$-n |
| XVII | OH | OH | OH | $CON(CH_3)(CH_2)_2COOH$ | $-C_6H_4-S-C_6H_{13}n$ |
| XVIII | OH | OH | OH | $COCH(CH_2C_6H_5)NH_2 \cdot HCl$ | DMTD |
| XIX | OH | OH | OH | $COCH_2NH_2 \cdot HCl$ | DMTD |
| XX | OH | OH | OH | $COOCH_2NH_2 \cdot HCl$ | $-C_6H_4OC_8H_{17}n$ |

EXAMPLE X

In similar operations, the following compounds in which R' is 9,11-trimethyldecyl are prepared.

| Compound No. | $R_1$ | $R_2$ | $R_3$ | $R_4$ | R |
|---|---|---|---|---|---|
| XXI | OH | H | OH | OH | $PO(ONa)_2$ |
| XXII | OH | H | H | H | $PO(ONa)_2$ |
| XXIII | H | H | H | H | $PO(ONa)_2$ |
| XXIV | H | OH | OH | OH | $PO(ONa)_2$ |
| XXV | OH | OH | H | OH | $PO(ONa)_2$ |
| XXVI | H | OH | H | H | $PO(ONa)_2$ |
| XXVII | OH | H | H | OH | $PO(ONa)_2$ |
| XXVIII | OH | OH | OH | OH | $SO_2ONa$ |
| XXIX | OH | OH | H | H | $SO_2ONa$ |
| XXX | H | OH | H | OH | $SO_2ONa$ |
| XXXI | OH | OH | OH | OH | $COCH_2COOH$ |
| XXXII | OH | OH | H | H | $COCH_2COOH$ |
| XXXIII | H | OH | H | OH | $COCH_2COOH$ |

In the following examples "Compound" followed by a Roman numeral designation refer to the compound in the example corresponding to the Roman numeral.

EXAMPLE XI 1000 compressed tablets each containing 500 mg of Compound A-1a are prepared from the following formulation:

| Compound | Grams |
|---|---|
| Compound A-1A (or formula I) | 500 |
| Starch | 750 |
| Dibasic calcium phosphate hydrous | 5000 |
| Calcium stearate | 2.5 |

The finely powdered ingredients are mixed well and granulated with 10% starch paste. The granulation is dried and compressed into tablets.

EXAMPLE XII 1000 hard gelatin capsules, each containing 500 mg of Compound are prepared from the following formulation:

| Compound | Grams |
|---|---|
| Compound A-1a (or I) | 500 |
| Starch | 250 |
| Lactose | 750 |
| Talc | 250 |
| Calcium stearate | 10 |

A uniform mixture of the ingredients is prepared by blending and used to fill two-piece hard gelating capsules.

EXAMPLE XIII 1000 hard gelatin capsules, each containing 500 mg of Compound IB are prepared from the following formulation:

| Compound | Grams |
|---|---|
| Compound III | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE XIV 250 ml of an injectable solution are prepared by conventional procedures having the following formulation:

| Dextrose | 12.5 g |
|---|---|
| Water | 250 mL |
| Compound A-1a (or I) | 400 mg |

The ingredients are blended and thereafter sterilized for use.

EXAMPLE XV 250 ml of an injectable solution are prepared by conventional procedures having the following formulation:

| Dextrose | 12.5 g |
|---|---|
| Water | 250 mL |
| Compound A-2a (or II) | 400 mg |

The ingredients are blended and thereafter sterilized for use.

EXAMPLE XVI

An ointment suitable for topical application may be prepared by intimately dispersing 13 mg of Compound A-2a in 1 g of commercially available polyethylene/hydrocarbon gel.

EXAMPLE XVII

An injectable solution similar to that of Example XIII except that Compound IV is substituted for Compound I is prepared.

EXAMPLE XVIII 1000 hard gelatin capsules, each containing 500 mg of Compound II are prepared from the following formulation:

| Compound | Grams |
|---|---|
| Compound II | 500 |
| Starch | 250 |
| Lactose | 750 |
| Talc | 250 |
| Calcium Stearate | 10 |

The components are uniformly blended and used to fill two-piece hard gelatin capsules.

EXAMPLE XIX

An aerosol composition may be prepared having the following formulation:

| | Per Canister |
|---|---|
| Compound I | 24 mg |
| Lecithin NF Liquid Concentrate | 1.2 mg |
| Trichlorofluoromethane, NF | 4.026 g |
| Dichlorodifluoromethane, NF | 12.15 g |

Starting Materials

Some of the lipopeptide starting materials are natural products, produced by fermentation, while some are semi-synthetic peptides which have been obtained by modification of the natural product.

Starting compound Z-1, in which U, V and W are OH and R' is 9,11-dimethyltridecyl, may be obtained by aerobically cultivating *Zalerion arboricola* ATCC 20868, or preferably *Z. arboricola* ATCC 20957, in a nutrient medium rich in mannitol until the desired Compound Z-1 is formed in the medium, thereafter extracting from the medium with methanol and then isolating by a series of chromatographic separations as more fully described in copending application Ser. No. 878,137, the teachings of which are incorporated by reference.

Starting compound Z-2 in which U and W are H and V is OH, or starting compound Z-4 in which U is H and V and W are OH, and R' is 9,11-dimethyltridecyl may be produced by a controlled reduction of Compound Z-1. The reduction is carried out by the addition of sodium cyanoborohydride to a solution of Compound Z-1 in trifluoroacetic acid or other strong acid solvent and allowing the reaction to take place with the formation of the mono- or bis-reduced product (Z-4 and Z-2 respectively) at ambient temperature; thereafter recovering from the reaction mixture and purifying by high performance liquid chromatography as more fully described in copending application Ser. No. 495,878, the teachings of which are incorporated by reference.

Starting Compound Z-3 in which U and V are H and W is OH and R' is 9,11-dimethyltridecyl may be obtained by aerobic cultivation of Z. arboricola ATCC 20958 in a medium enriched in mannitol until the desired compound is produced and thereafter extracting with methanol and purifying by chromatography, preferably HPLC as more fully described in copending application Ser. No. 495,653, the teachings of which are incorporated by reference.

Starting compounds in which R' is other than 9,11-tridecyl may be obtained by deacylating the appropriate lipopeptide in which R' is 9,11-tridecyl by subjecting said compounds in a cultivation medium to a deacylating enzyme, said enzymes obtained first by cultivating a microorganism of the family Pseudomondaceae or Actinoplanaceae, until substantial deacylation occurs and then recovering the deacylated cyclopeptide and thereafter acylating the isolated nucleus with an appropriate active ester R'COX to obtain starting compound Z in which R' is other than 9,11-dimethyltridecyl.

Other starting compounds, e.g., where (a) $R_1$, $R_2$, $R_3$ and $R_4$ are H; (b) $R_1$ is OH and $R_2$, $R_3$ and $R_4$ are H; and (c) $R_2$ is H and $R_1$, $R_2$ and $R_3$ are OH and R' is 9,11-dimethyltridecyl may be obtained by cultivating Z arboricola ATCC 20868 as described in copending application Ser. No. 374,416 filed Jun. 30, 1989.

The deacylation is carried out by subjecting the starting lipopeptide, Compound Z, when R'=DMTD in a nutrient medium or a buffer solution to a deacylating enzyme obtained from or present in intact cells of the microorganism of the family Actinoplanaceae or Pseudomondacea generally at a temperature in the range of 20° to 40° C., preferably 25° to 30° C. at a pH between 5.0 and 8.0, with agitation and aeration, for from 16 to 48 hours if Pseudomondacea is used or from 40 to 60 hours if Actinoplanacea is used until the deacylation is judged to be complete as indicated by the disappearance of the anti-Candida activity of the substrate or as determined by analytical HPLC assay from a previously determined standard.

The reacylation of the deacylated cyclohexapeptide may be carried out by intimately contacting the deacylated compound with an active ester,

in a solvent such as water, dioxane, dimethylformamide, and the like. R' is as previously defined and X is any appropriate leaving group such as chloride, fluoride, bromide, cyanide, trichlorophenoxide, 1-benzotriazolate and the like. The reaction is carried out at room temperature, conveniently overnight. At the end of this time, the solvent is removed in vacuo and the residue triturated with ether and methylene chloride and then filtered. The product may be purified by reverse phase HPLC using acetonitrile/water as eluting agent. The fractions containing the acylated product may be determined by C albicans assay or by U.V.

What is claimed is:

1. A compound having the formula:

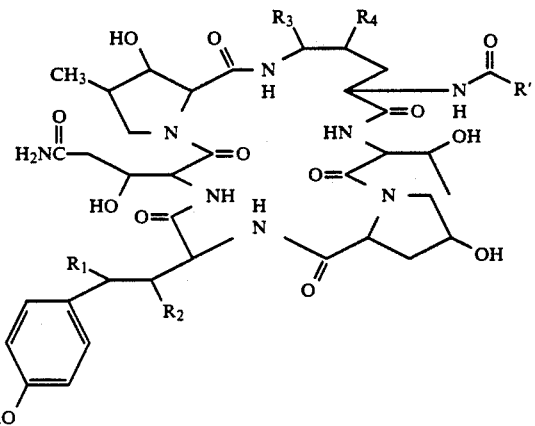

wherein $R_1$, $R_2$, $R_3$ and $R_4$ are independently H or OH;

R' is $C_5$-$C_{23}$ alkyl, $C_5$-$C_{23}$ alkenyl, $C_5$-$C_{23}$ alkynyl or aryl; and R is an acyl, phosphono or sulfo radical which possesses a charged group at a neutral pH.

2. A compound having the formula

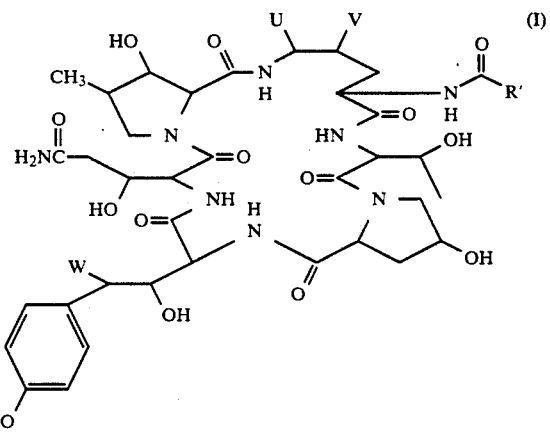

wherein

U, V and W are independently H or OH, selected from those in which (1) U, V and W are all OH; (2) U and W are H and V is OH; (3) U and V are H and W is OH;

R' is $C_5$-$C_{23}$ alkyl, $C_5$-$C_{23}$ alkenyl, $C_5$-$C_{23}$ alkynyl or aryl; and R is (1) PO₃AH wherein A is H, $C_1$-$C_6$ alkyl, phenyl or substituted phenyl wherein the substituent may be alkyl, alkyloxy, alkylthio, or alkylamino or a Li, Na, K, Mg and Ca cation salt thereof;

(2) SO₃H or cation salt thereof as defined in (1)

(3) $COC_nH_{2n}CO_2H$ wherein n is 1 to 6 or a cation salt thereof as defined in (1)

(4) $CONAC_nH_{2n}CO_2H$ wherein A is as defined in (1), n is 1 to 6, or a cation salt thereof as defined in (1)

(5) $COOC_nH_{2n}CO_2H$ wherein n is 1 to 6, or a cation salt thereof as defined in (1)

(6) $CONA(CHB)CO_2H$ wherein B is a residue of an amino acid, or a cation salt thereof; as defined in (1)

(7) $COCHBNR_1R_2$ wherein B is a residue of an amino acid, $R_1$ and $R_2$ independently are H, $C_1$-$C_6$ alkyl, and phenyl, and acid addition salts thereof;

(8) $CONAC_nH_{2n}NR_1R_2$ wherein A is as defined in (1), $R_1$ and $R_2$ independently are as defined in (7), n is 2 to 6, and acid addition salts thereof;

(9) $COOC_nH_{2n}NR_1R_2$ wherein $R_1$ and $R_2$ independently are as defined in (7), n is 2 to 6, and acid addition salts thereof; and

(10) $COC_nH_{2n}NR_1R_2$ wherein $R_1$ and $R_2$ independently are as defined in (7), n is 1 to 6 and acid addition salts thereof.

3. An antimicrobial composition comprising a compound of claim 1 in admixture with a biologically inert carrier.

4. A composition according to claim 3 which is an antifungal composition.

5. A composition according to claim 4 which is useful for the treatment of mycotic infections.

6. A composition according to claim 3 which is an antiprotozoal composition.

7. A composition according to claim 6 which is useful for the treatment of *Pneumocystis carinii* infections.

8. A method for treating patients with mycotic infections comprising administering an effective therapeutic amount of a compound of claim 1.

9. A compound according to claim 2 where U, V and W are all OH, R is phosphono, and R' is 9,11-dimethyltridecyl and cation salts thereof.

10. A compound according to claim 2 where U and W are H and V is OH, R is phosphono, and R' is 9,11-dimethyltridecyl and cation salts thereof.

11. A compound according to claim 2 where U and V is H and W is OH, R is phosphono, and R' is 9,11-dimethyltridecyl and cation salts thereof.

12. A method for preventing or treating subjects infected with or susceptible to being infected with *Pneumocystis carinii* which comprises administering an effective preventative or therapeutic amount of the compound of claim 1.

* * * * *